United States Patent [19]

Funakoshi et al.

[11] Patent Number: 5,331,949
[45] Date of Patent: Jul. 26, 1994

[54] ENDOSCOPE HAVING ILLUMINANCE RATIO ADJUSTING DEVICE BETWEEN MOVING AND STILL PICTURE IMAGES

[75] Inventors: Toshio Funakoshi; Katsuya Kikuchi, both of Tochigi, Japan

[73] Assignee: Kabushiki Kaisha Toshiba, Kawasaki, Japan

[21] Appl. No.: 728,055

[22] Filed: Jul. 8, 1991

Related U.S. Application Data

[63] Continuation of Ser. No. 409,661, Sep. 20, 1989, abandoned.

[30] Foreign Application Priority Data

Sep. 20, 1988 [JP] Japan .................. 63-233439

[51] Int. Cl.⁵ ............................... A61B 1/06
[52] U.S. Cl. ................................ 128/6; 348/69; 348/221
[58] Field of Search ............ 128/6, 4; 358/98; 362/3, 4, 5; 354/62, 132

[56] References Cited

U.S. PATENT DOCUMENTS

| | | | |
|---|---|---|---|
| 4,366,529 | 12/1982 | Takahashi et al. | 128/6 |
| 4,384,775 | 5/1983 | Hosoda | 128/6 |
| 4,416,524 | 11/1983 | Takayama | 128/6 |
| 4,602,281 | 7/1986 | Nagasaki et al. | 128/6 |
| 4,791,480 | 12/1988 | Muranaka | 128/6 |
| 4,803,550 | 2/1989 | Yabe et al. | 128/6 |
| 4,821,116 | 4/1989 | Nagasaki et al. | 128/6 |
| 4,866,526 | 9/1989 | Ams et al. | 128/6 |
| 4,872,029 | 10/1989 | Kato | 128/6 |

FOREIGN PATENT DOCUMENTS

| | | |
|---|---|---|
| 3818104 | 12/1988 | Fed. Rep. of Germany . |
| 3903150 | 8/1989 | Fed. Rep. of Germany . |
| 60-66220 | 4/1985 | Japan . |
| 01-181822 | 8/1989 | Japan . |

Primary Examiner—William H. Grieb
Assistant Examiner—Jessica J. Harrison
Attorney, Agent, or Firm—Foley & Lardner

[57] ABSTRACT

An endoscope in which moving and still picture image pickup operations are alternatively carried out, and a light source emits either a continuous light or a pulsed light in the moving or still picture image pickup operations, a detector detects illuminances of moving and still picture images in the moving and still picture image pickup operations to obtain an illuminance ratio between the moving and still picture images, and the illuminance ratio is adjusted to a certain value by an adjuster on the basis of the illuminance ratio detected by the detector.

13 Claims, 6 Drawing Sheets

ENDOSCOPE HAVING ILLUMINANCE RATIO ADJUSTING DEVICE BETWEEN MOVING AND STILL PICTURE IMAGES

This application is a continuation of application Ser. No. 07/409,661, filed Sep. 20, 1989 now abandoned.

BACKGROUND OF THE INVENTION

1. Field of the Invention

The present invention relates to an endoscope including a device for adjusting an illuminance ratio between moving and still picture images.

2. Description of the Background Art

In a conventional endoscope, when picture images are picked up by using continuous light, reproduced picture images are blurred by a freezing operation, and the resolving power of the reproduced picture images is extremely reduced. In order to solve this problem, a pulsed light is used in the freezing operation. That is, in this case, when a moving picture image pickup is carried out, continuous lighting is performed by applying a DC current to a light source, and a time width of one frame is coincident with a radiation time width of the same. In turn, when a still picture image pickup is carried out in response to a freezing operation, a light pulse extending over the boundary between adjacent odd and even fields is emitted by a light source every one frame.

In this case, when the moving and still picture images are picked up and the illuminance of the moving picture image is equal to that of the still picture image, there is no difference in brightness between the moving and still picture images on a display, and thus it is very convenient and easy for an operator to observe the displayed picture images.

In order to adjust the luminous energy or illuminance ratio between the moving and still picture images to be the same or close to each other, one of predetermined values of a tube current to be applied to a lighting tube such as a xenon lamp of a light source is elected to change the light intensity of the light source. That is, in this case, the light intensity of the light source during pickup of the moving picture image is determined by selecting one of the fixed tube current values.

However, after the lighting tube of the light source has been used for a long period of time, its light output becomes gradually lowered, and thus a change arises in the light intensity ratio initially determined at an entrance end of a light guide of a scope between the continuous DC current lighting for picking up the moving picture image and the pulsed lighting for picking up the still picture image in the light source. Hence, a change in brightness between the moving and still picture images appears on the monitor, and the difference in brightness between the moving and still picture images is gradually increased.

SUMMARY OF THE INVENTION

Accordingly, it is an object of the present invention to provide an endoscope, free from the aforementioned defects and disadvantages of the prior art, which is capable of adjusting an illuminance ratio between moving and still picture images picked up in moving and still picture imagings until a light source becomes useless due to a remarkable deterioration, malfunction, accident or the like.

It is another object of the present invention to provide an endoscope, free from the aforementioned defects and disadvantages of the prior art, which is capable of adjusting a brightness ratio between moving and still picture images picked up in moving and still picture imagings until a light source becomes useless due to significant deterioration, trouble, accident or the like.

It is still another object of the present invention to provide an endoscope, free from the aforementioned defects and disadvantages of the prior art, which is capable of making illuminance of moving and still picture images equal, the images being picked up in moving and still picture imagings, until a light source becomes useless due to a deterioration, trouble, accident or the like.

It is a further object of the present invention to provide an endoscope, free from the aforementioned defects and disadvantages of the prior art, which is capable of making brightness of moving and still picture images equal, the images being picked up in moving and still picture imagings, until a light source becomes useless due to a deterioration, trouble, accident or the like.

In accordance with one aspect of the present invention, there is provided an endoscope having a scope, in which moving and still picture image pickup operations are alternatively carried out, comprising light source means for emitting either a continuous light or a pulsed light in the moving or still picture image pickup operations, means for detecting the brightness of moving and still picture images in the moving and still picture image pickup operations to obtain an illuminance ratio between the moving and still picture images, and means for adjusting the illuminance ratio to a certain value on the basis of the illuminance ratio detected by the detecting means.

BRIEF DESCRIPTION OF THE DRAWINGS

The above and other objects, features and advantages of the present invention will more fully appear from the following description of the preferred embodiments with reference to the accompanying drawings, in which.

DESCRIPTION OF THE PREFERRED EMBODIMENTS

Figure 1:
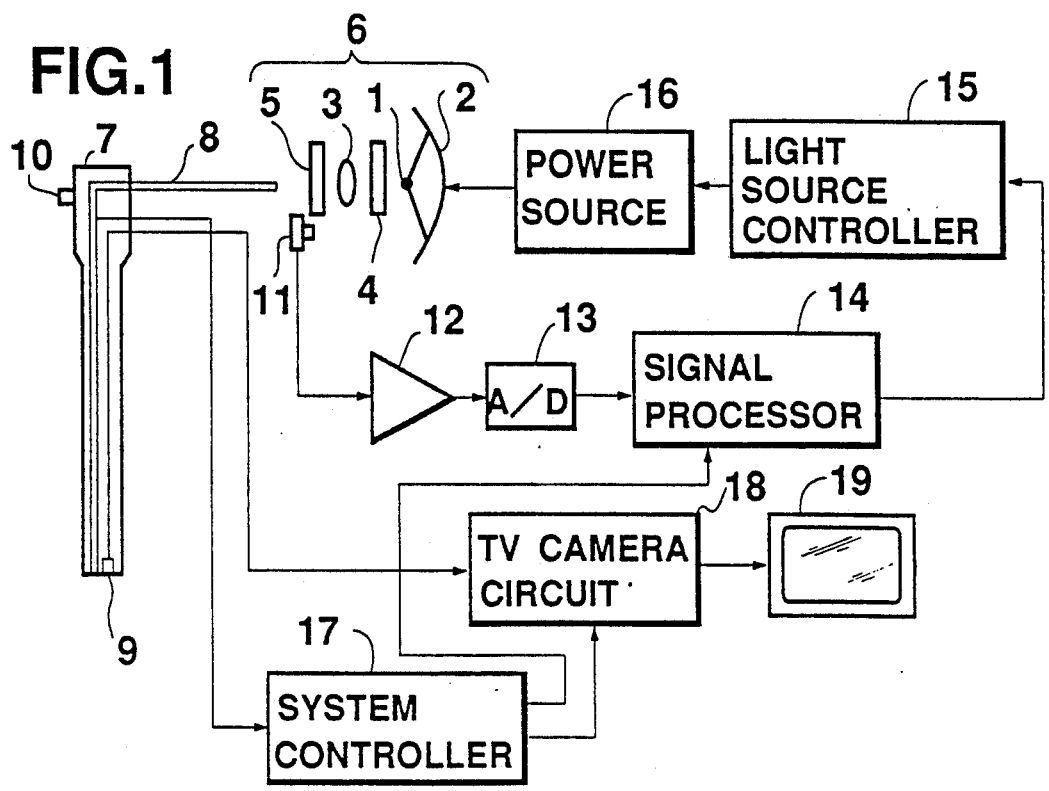
FIG. 1 is a block diagram of one embodiment of an endoscope according to the present invention.

Referring now to the drawings, wherein like reference characters designate like or corresponding parts throughout the several views, there is shown in FIG. 1 one embodiment of an endoscope according to the present invention.

In FIG. 1, a xenon lamp 1, a reflector 2 for the lamp 1, a condenser lens 3, luminous energy control devices 4 and 5 such as light filters constitute a light source 6. The light emitted by the light source 6 is incident on a light entrance end of alight guide 8 of a scope 7 having a solid-state image pickup device 9 such as CCD (charge coupled devices) arranged in the end and a freeze switch 10. A photo detector 11 is arranged in the vicinity of a light path connecting the light source 6 to the light guide 8. The photo detector 11 detects a part of the luminous energy of the light emitted by the light source 6 and outputs a signal corresponding to the intensity of the light to an analog-digital (A/D) converter 13 via an amplifier 12, and the A/D converter 13 sends digital signals to a signal processor 14.

The signal processor 14 acts as lighting condition detection means and tube current determination means, and outputs a tube current control signal to a light source controller 15, as hereinafter described in detail. The light source controller 15 controls a power source 16 for driving the light source 6 according to the tube current control signal fed from the signal processor 14 to control the radiation luminous energy of the light source 6. A system controller 17 controls the entire system of the endoscope.

In the scope 7, the light incident on the light inlet end of the light guide 8 is led to the end of the scope 7 through the light guide 8, and irradiates the object (not shown) to be observed. While the object is illuminated by the light emitted from the end of the scope 7, the picture image of the object is picked up by the image pickup device 9. The image pickup device 9 outputs a photoelectrically transduced signal VP to a TV camera circuit 18, and the TV camera circuit 18 converts the signal VP and outputs a video signal to a display 19 for displaying the object thereon.

The photo detector 11 is arranged close to the light entrance end of the light guide 8 of the scope 7 and detects the leaked partial light which is not incident to the light guide 8 in the light source 6. The luminous energy of the partial light detected by the photo detector 11 is proportional to the light to be irradiated to the object. Hence, the signal processor 14 receives the signal output from the photo detector 11 via the amplifier 12 and the A/D converter 13, this output signal corresponding to the luminous energy of the light to be irradiated to the object during the pickup of the moving or still picture image.

The operation of the endoscope described above will now be described in detail in connection with FIGS. 2 to 4.

Figure 2:
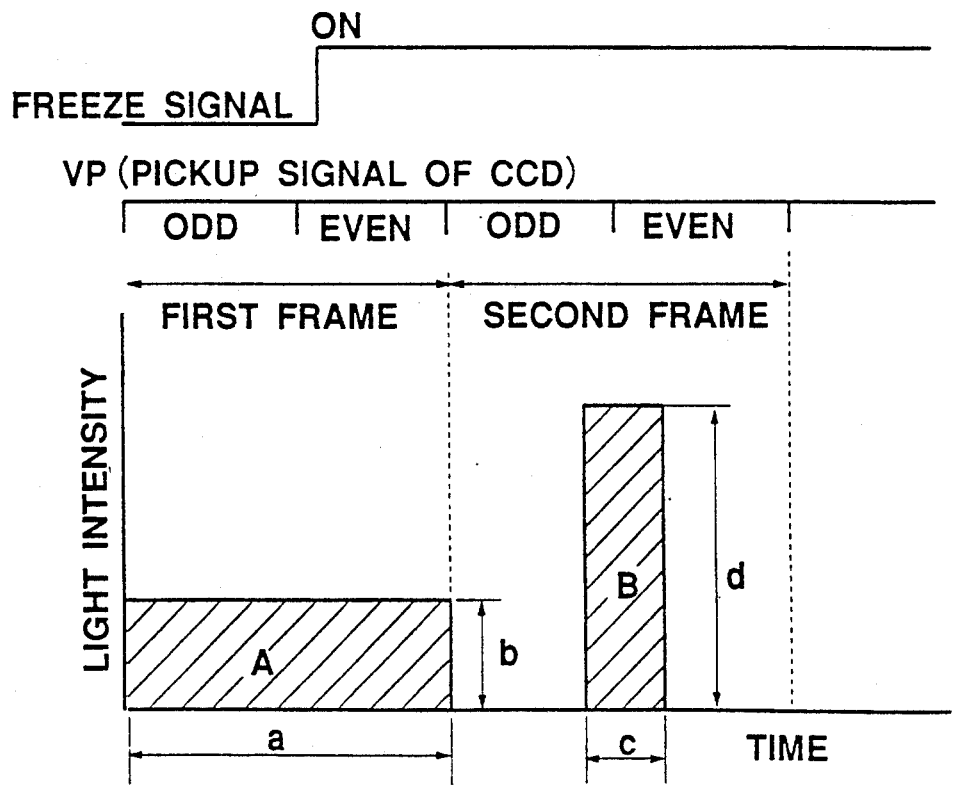
FIG. 2 is a timing chart schematically showing a lighting control of a light source shown in FIG. 1.
Figure 3:
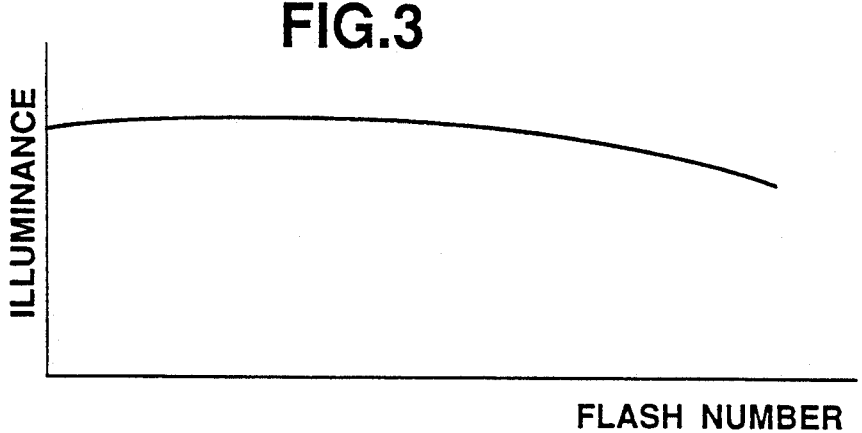
FIG. 3 is a graphical representation showing an intensity curve of a light pulse emitted by a light source shown in FIG. 1.

In FIG. 2, A is a radiation area of one frame of the continuous DC current light in the moving picture image pickup, and B is a radiation area of one frame of the pulsed light in the still picture image pickup. When the moving picture image is picked up in real time, for instance, the continuous illumination is carried out, where the time width extending over the odd and even fields is coincident with the time width of the radiation area A in the first frame.

When the freeze switch 10 of the scope 8 is switched on in the first frame time range, the system controller 17 outputs the freeze signal to the signal processor 14, and the signal processor 14 sends the tube current control signal to the light source controller 15. Then, the light source controller 15 controls the power source 16 to allow the light source 6 to emit the pulsed light extending over the boundary of the adjacent odd and even fields, as indicated by B in FIG. 2.

In this case, the areas $(a \times b)$ and $(c \times d)$ of the respective radiation areas A and B indicate the radiation luminous energy or illuminance in each frame. When the moving picture image pickup is changed to the still picture image pickup, the picture image on the display suddenly glows bright in the case of $(a \times b) < (c \times d)$, and, in turn, suddenly gets dark in the case of $(a \times b) > (c \times d)$.

In order to make the brightness of the picture images on the display equal in the moving and still picture imagings, the radiation area A must be equal to the radiation area B. That is, $(a \times b) = (c \times d)$, or $a/c = d/b$. Now, $a = 33.3$ msec and $c = $ constant such as 2 msec. Thus, the light intensity of the light source 6 should be adjusted to $d/b = 33.3/2 \approx 16.7$ (constant, the ratio $$\frac{d}{b}$$

representing the ratio of the intensity of the light source during still image pickup to that during moving image pickup).

In view of this, it should be avoided that the tube current to be supplied to the light source 6 is fixed to a certain value. When the tube current is determined to a fixed value, for instance, as shown in FIG. 3, the intensity (= d in FIG. 2) of the light pulse emitted by the light source 6 is gradually reduced due to the deterioration of the light source 6 as the lighting tube is used for a long period of time and the light pulse flashing number is increased. Further, the intensity of the light pulse may be also varied due to damage of the lighting tube.

That is, after the tube current for emitting the light pulse from the light source is fixed at the initial time, the relation of the radiation area A = radiation area B in FIG. 2 will be gradually destroyed by repeatedly carrying out the freezing operation.

When $(A - B)/A$ is within several percent such as 3%, the brightness difference on the display can not be sensed. In this embodiment, in the signal processor 14, since a and c of the radiation areas A and B are fixed, as described above, the luminous energy or illuminance of the radiation areas A and $B = (a \times b)$ and $(c \times d)$ or the light intensity b and d thereof during the freezing at time n is firstly detected, and then the tube current during the next freezing at time $n+1$ is determined on the basis of the detected values as hereinafter described.

Figure 4:
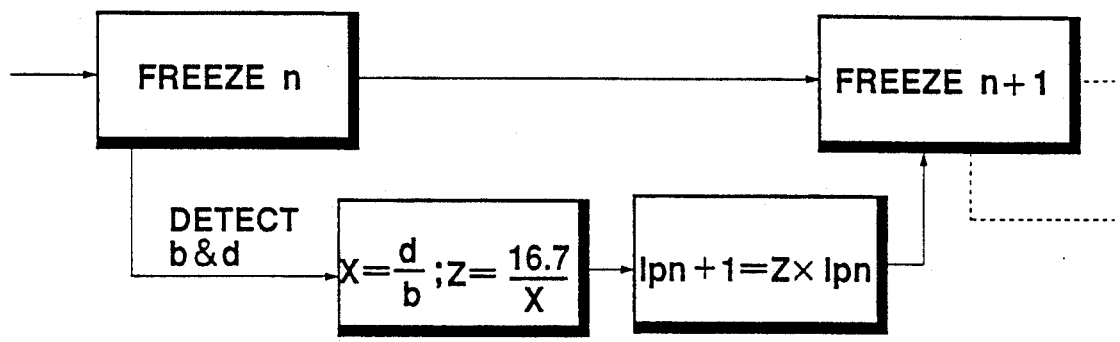
FIG. 4 is a block diagram of one operation in a signal processor shown in FIG. 1.

In FIG. 4, there is shown one embodiment of a feedback control operation in the signal processor 14. At the freezing at time n, the intensity b and d of the light is detected and $X = d/b$ is obtained. Then, $Z = 16.7/X$ is operated when c of the radiation area B is 2 msec. Assuming that the tube currents $I_{pn}$ and $I_{pn+1}$ at the freezings at times n and $n+1$, respectively, the tube current $I_{pn+1}$ at the freezing at time $n+1$ can be operated according to the following formula:

$$I_{pn+1} = Z \times I_{pn}$$

The signal processor 14 outputs a tube current control signal representing the obtained tube current Ipn+1 at the next freezing of n+1 time to the light source controller 15. Then, the light source controller 15 controls to drive the power source 16 at the next freezing at time n+1 according to the tube current Ipn+1 in order to make the brightness of the moving and still picture images equal.

Then, the intensity b and d at the freezing at time n+1 is detected, and then the tube current Ipn+2 at the freezing at time n+2 is obtained in the signal processor 14 in the same manner as described above. In the light source controller 15, the tube current is then replaced by the new value Ipn+2. The same operation is repeated every freezing operation.

Figure 5:
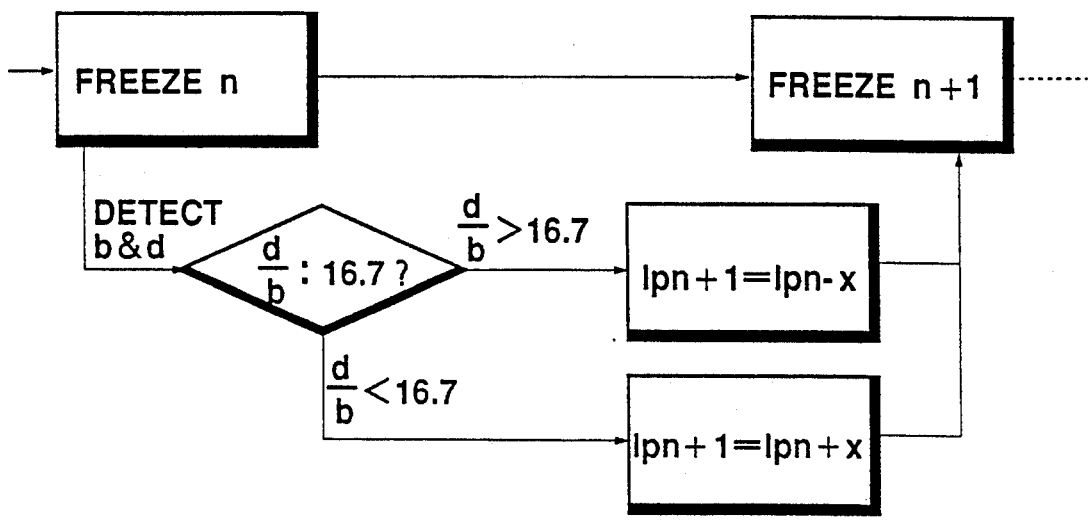
FIG. 5 is a block diagram of another operation of the signal processor shown in FIG. 1.

In FIG. 5, there is shown another embodiment of the feedback control in the signal processor 14. In this embodiment, it is perceived that the brightness variation on the display can not be sensed when $(A-B)/A$ is within several percent. That is, the intensity b and d of the light is detected at the freezing at time n, and then it is discriminated whether d/b is larger than 16.7 or not.

When d/b>16.7, the tube current Ipn+1 at the next freezing at time n+1 is obtained by reducing a certain current value x from the tube current Ipn at the freezing of n time in the following formula:

$$Ipn+1 = Ipn - x$$

In turn, when d/b<16.7, the tube current Ipn+1 at the next freezing at time n+1 is obtained by adding the current value x to the tube current Ipn at the freezing at time n in the following formula:

$$Ipn+1 = Ipn + x$$

In this case, the current value x may be so determined that, even when the present tube current Ip is ideal value and the current value x is added to the ideal tube current Ip, the value (Ip+x) may be within a permissible range where uneven brightness between the moving and still picture images can not be sensible on the display.

The signal processor 14 outputs a tube current control signal representing the obtained tube current (Ipn-x) or (Ipn+x) at the next freezing at time n+1 to the light source controller 15. Then, the light source controller 15 controls to drive the power source 16 at the next freezing at time n+1 to make the brightness of the moving and still picture images to be equal in the same manner as described above.

As described above, according to the present invention, it is readily understood that brightness of moving and still picture images picked up in moving and still picture imagings can be automatically adjusted to be equal until a light source becomes useless due to a remarkable deterioration, a trouble, an accident or the like, and that illuminance of the moving and still picture images can be also automatically adjusted to be equal. It is also readily understood that a brightness ratio between moving and still picture images picked up in moving and still picture imagings can be automatically adjusted and an illuminance ratio between the moving and still picture images can be also automatically adjusted until a light source becomes useless due to a remarkable deterioration, a trouble, an accident or the like.

Figure 6:
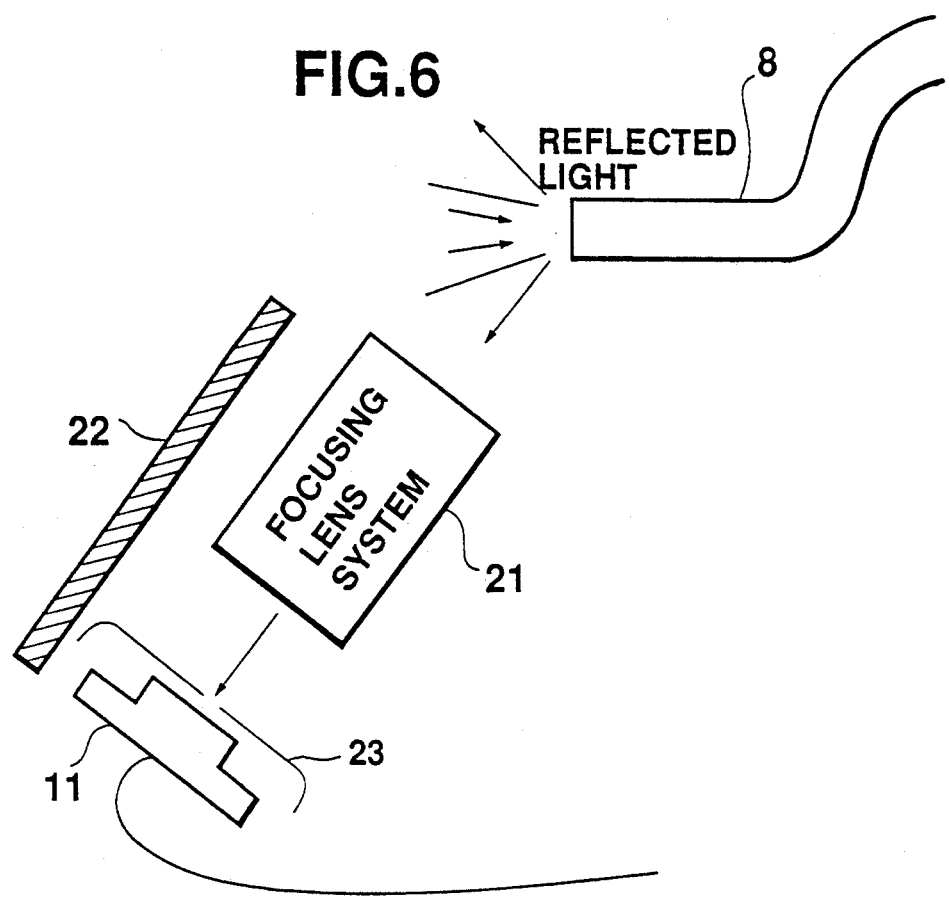
FIG. 6 is a schematic view of another arrangement of a photo detector according to the present invention.

In FIG. 6, there is shown another arrangement of a photo detector 11 which receives a partial light reflected by the inlet end of the light guide 8 through a focusing lens system 21 and a cover plate 23 having an opening. A light shield plate 22 may be also provide for preventing the light from coming into the photo detector 11. In this case, the photo detector 11 can detect the light intensity precisely proportional to the output light of the light guide 8.

Figure 7:
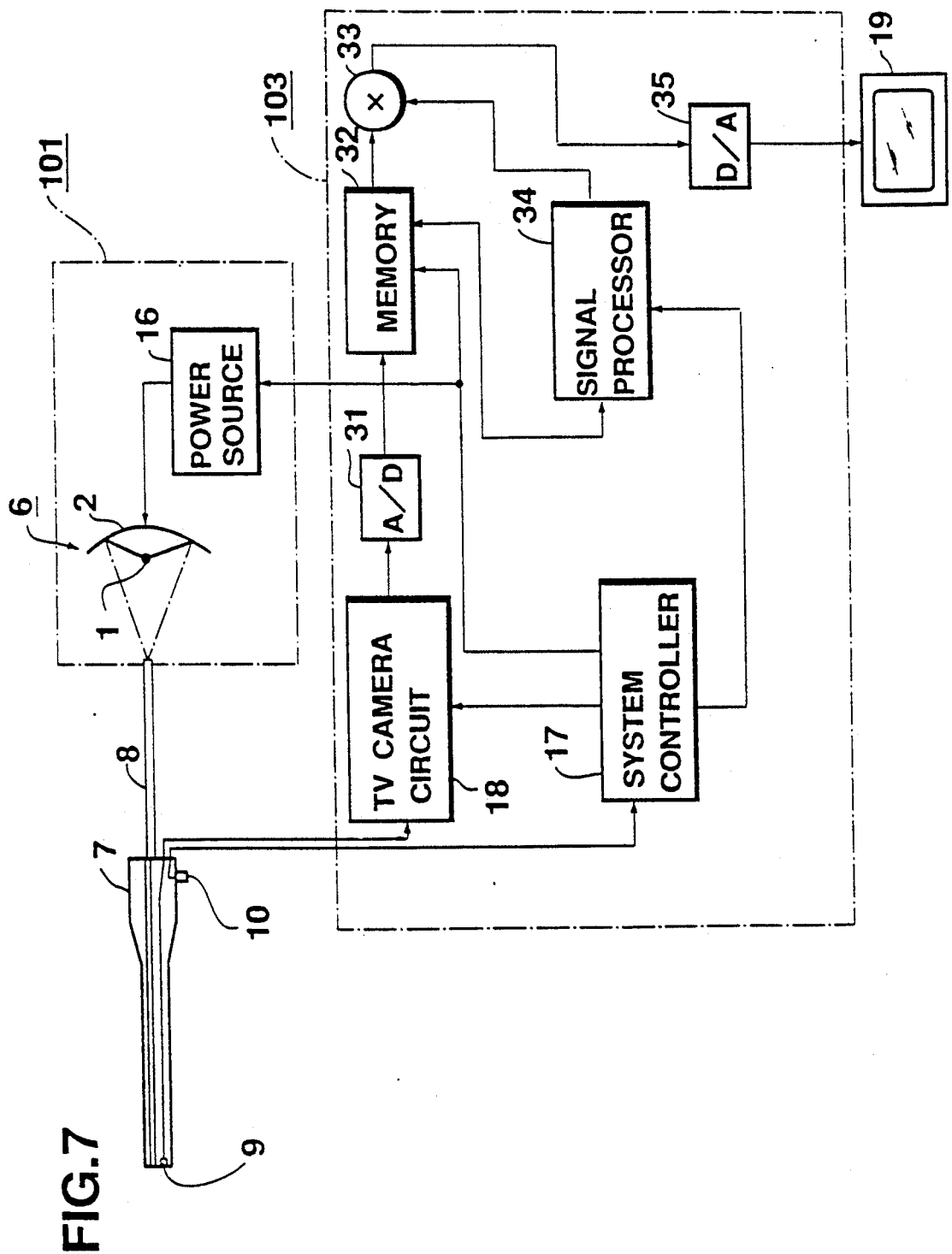
FIG. 7 is a block diagram of a second embodiment of an endoscope according to the present invention.

In FIG. 7, there is shown a second embodiment of an endoscope according to the present invention, having a similar structure to the first embodiment shown in FIG. 1.

In this embodiment, the endoscope comprises a scope 7, a light source section 101 and a processing body section 103. The light source section 101 includes a light source having a xenon lamp 1 and a reflector 2, and a power source 16, and the processing body section 103 includes a system controller 17, a TV camera circuit 18, an A/D converter 31, a memory 32, a multiplier 33, a signal processor 34 and a digital-analog (D/A) converter 35, as hereinafter described in detail.

Figure 8:
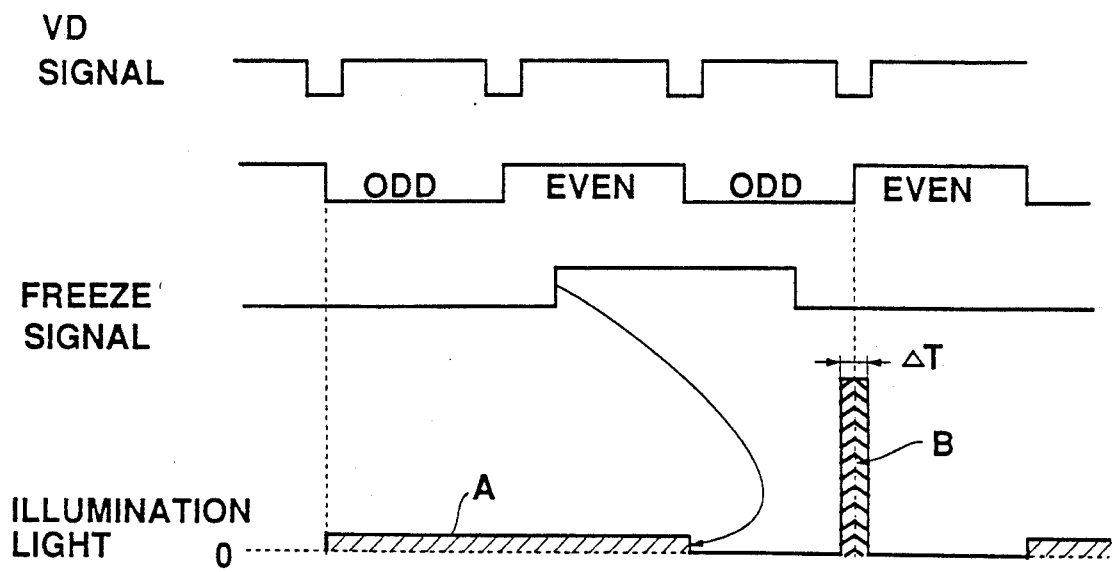
FIG. 8 is a timing chart schematically showing an operation for obtaining a frame of picture image in the endoscope shown in FIG. 7.

FIG. 8 shows, like FIG. 2, a VD signal, a freeze signal and an illumination pulse, in which A and B represent areas or luminous energy or illuminances of one frame of a continuous light and a pulsed light in the moving and still picture image pickup modes, respectively, and $\Delta T$ is the time length of the pulsed light in a freezing operation.

Figure 9:
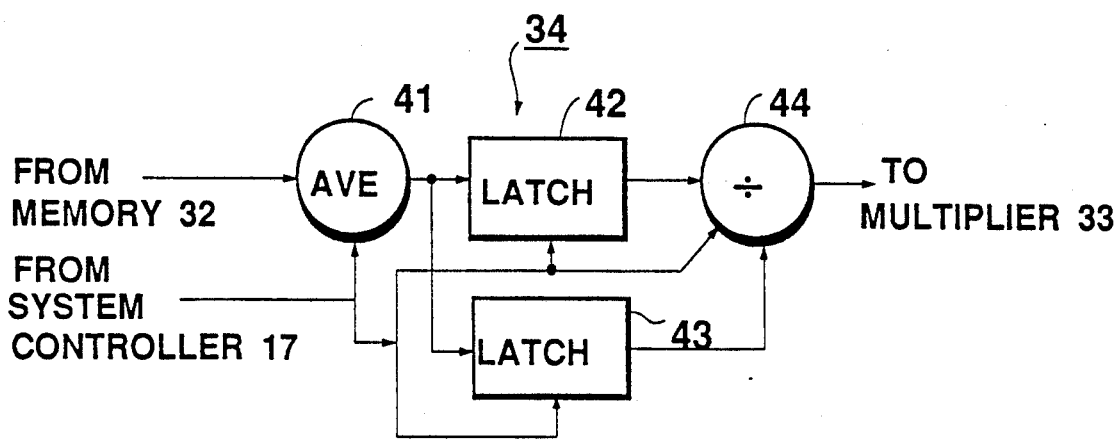
FIG. 9 is a block diagram of a signal processor shown in FIG. 7.

In FIG. 9, there is shown one embodiment of the signal processor 34 for operating the ratio between the illuminances A and B of one frame of the continuous and pulsed lights of the illuminance light, the signal processor 34 comprising a summing circuit (SUM) 41, a pair of latch circuits (LATCHs) 42 and 43 for the illuminances A and B of the moving and still picture image pickup modes, and a divider circuit 44, as hereinafter described in detail.

In a usual moving picture pickup operation, the light source emits the continuous illumination light to the light guide 8 of the scope 7, and the image pickup device 9 picks up the light reflected by the object to be observed. The TV camera circuit 18 receives the image signals fed from the image pickup device 9 of the scope 7, converts the image signals to color video signals, and sends the color video signals to the A/D converter 31. The A/D converter 31 converts the color video signals to digital color video signals, and outputs the digital color video signals to the memory 32 for once storing the signals therein. Then, the digital color video signals are read out of the memory 32 to be sent to the D/A converter 35 through the multiplier 33, and are converted to the analog color video signals in the D/A converter 35. The analog color video signals are sent from the D/A converter 35 to the display 19 for displaying the moving picture images thereon.

Now, when the freeze switch 10 is switched on, as shown in FIG. 8, the freeze signal is output, and the light source is changed from a continuous light illumination mode to a pulsed light illumination mode from the beginning of one odd field section soon after the leading timing of the output freeze signal. That is, from the beginning of this odd field section, the illuminance is changed from on state to off state, and then a strong light pulse is emitted from the light source for a quite short period $\Delta T$ between the end portion of this odd field section and a beginning portion of a next even field section adjacent thereto, i.e., extending over the boundary between the adjacent odd and even field sections. Thereafter, the illuminance is changed to off to the end of this even field section, and then the continuous light illumination mode becomes on or starts again from the followed odd field section.

In this case, initially, the illuminance A of the moving picture pickup mode is adjusted to be equal to the illuminance B of the still picture pickup mode, but a difference arises between the illuminances A and B as the light source is used for a long period of time. Then, the ratio between the illuminances A and B is operated, and, when the illuminance ratio is not "one", the illuminance ratio is corrected to "one" by using the operated illuminance ratio.

In this embodiment, the signal processor 34 operates the ratio between the illuminances A and B of the illumination pulse. In the signal processor 34, the moving picture image data, output from the memory 32, for several picture elements just before the freezings are sent to the AVE 41 and are averaged therein to obtain an average value. The average value is stored in the LATCH 42. Another average value for the still picture image data at the freezings is obtained in the AVE 41 and is then stored in the LATCH 43 in the same manner as the moving picture average value described above.

For example, when the still picture image illuminance B is 1.1 times larger than the moving picture image illuminance A, the divider circuit 44 outputs a value 1.1 to the multiplier 33. In the multiplier 33, a reciprocal number, e.g., 1/1.1 in this case, of the output of the divider circuit 44 is multiplied as a correction value to the still picture image data fed from the memory 32 in order to correct the difference between the moving and still picture image illuminances and to correct difference in brightness between the moving and still picture image pickup operations. The corrected color video signals are sent from the multiplier 33 to the display 19 through the D/A converter 35. The display 19 displays a still picture image according to the analog color video signals fed from the D/A converter 35. During the display of the still picture image on the display 19, the input of the another picture image data into the memory 32 is prevented, and the picture image data stored in the memory 32 is repeatedly read out thereof for the display of the picture images. In this case, the operation relating to the freeze process is controlled by the system controller 17. In this embodiment, the same effects and advantages as those obtained in the first embodiment can result.

Although the present invention is applied to an endoscope having a solid-state image pickup device such as a CCD in the end of a scope, of course, the present invention can be applicable to an endoscope with a fiber scope and an optical camera device in its end portion.

Figure 10:
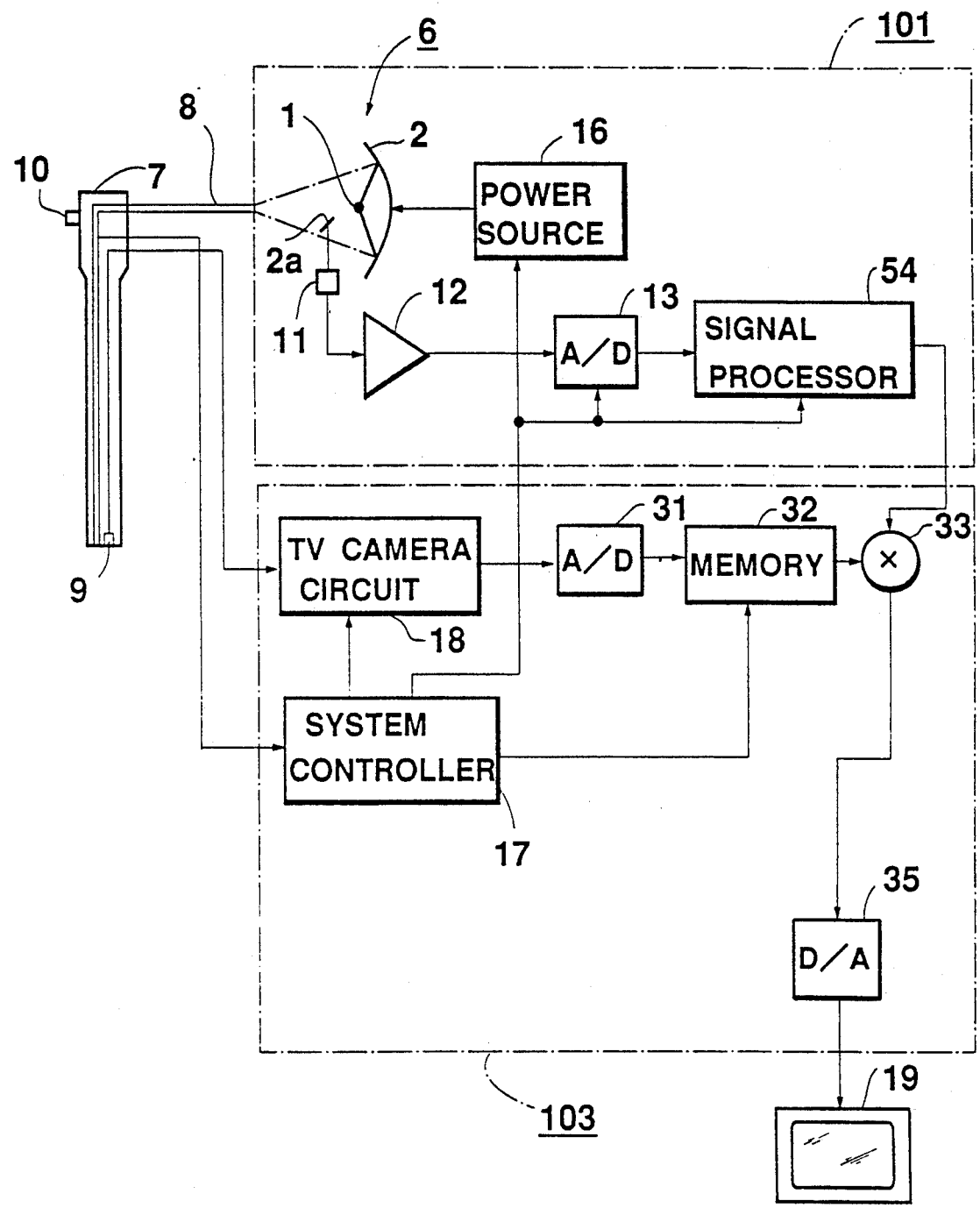
FIG. 10 is a block diagram of a third embodiment of an endoscope according to the present invention.

In FIG. 10, there is shown a third embodiment of an endoscope according to the present invention, having a similar structure to the second embodiment shown in FIG. 7.

In this embodiment, as shown in FIG. 10, the endoscope comprises a scope 7, a light source section 101 and a processing body section 103. The light source section 101 includes a light source 6 having a xenon lamp 1, a reflector 2 and a half mirror 2a, a photoelectric device 11, an amplifier 12, an A/D converter 13, a power source 16 and a signal processor 54 for operating a ratio between moving and still picture image illuminances A and B of an illumination light, and the processing body section 103 includes a system controller 17, a TV camera circuit 18, an A/D converter 31, a memory 32, a multiplier 33 and a D/A converter 35, as hereinafter described in detail.

In this case, the TV camera circuit 18 receives image signals from the image pickup device 9 of the scope 7, converts the image signals to analog color video signals, and sends the analog color video signals to the A/D converter 31. The A/D converter 31 converts the analog color video signals to digital color video signals, and outputs the digital color video signals to the memory 32 for once storing these signals therein. The digital color video signals are read out of the memory 32 and are fed to the D/A converter 35 through the multiplier 33 in the same manner as the second embodiment.

In the freezing operation, the multiplier 33 multiplies the output of the memory 32 by a correction value on the basis of the output signal of the signal processor 54, as hereinafter described in detail, and sends the corrected color video signals to the display 19 through the D/A converter 35. The display 19 displays a picture image according to the analog color video signals fed from the D/A converter 35.

Figure 11:
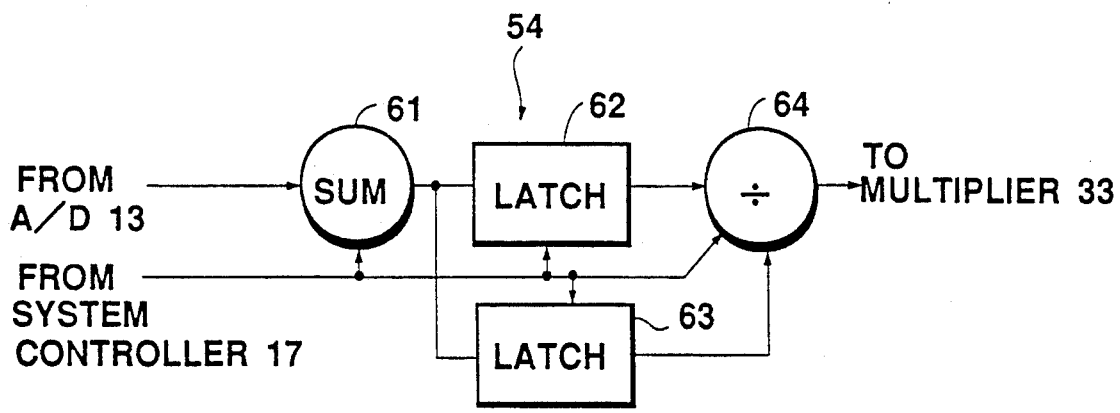
FIG. 11 is a block diagram of a signal processor shown in FIG. 10.

In FIG. 11, there is shown one embodiment of the signal processor 54 for operating a ratio between moving and still picture image illuminances A and B of the illumination light, which comprises a summing circuit (SUM) 61, a pair of latch circuits (LATCHs) 62 and 63 for the moving and still picture image illuminances A and B, and a divider circuit 64, as hereinafter described in detail.

Now, when the freeze switch 10 is switched on, the freeze signal is output, and the light source 6 is changed from a continuous light radiation mode to a pulsed light radiation mode in the same manner as the second embodiment described above.

In the signal processor 54, the ratio between the moving and still picture image illuminances A and B is operated as follows. In the moving picture image pickup operation, the digitalized output signals of the A/D converter 13 are summed in the SUM 61, and the summed result is stored in the LATCH 62. In the still picture image pickup operation, the digitalized output signals of the A/D converter 13 are summed in the SUM 61, and the summed result is stored in the LATCH 63. The summed results of the LATCHs 62 and 63 are sent to the divider circuit 64 in which the ratio of the summed results is calculated.

For instance, when the moving picture image illuminance A is 1.1 times larger than that of the still picture image illuminance B, the divider circuit 64 outputs a value 1.1 to the multiplier 33. In the multiplier 33, a reciprocal number, e.g., 1/1.1 in this case, of the output of the divider circuit 64 is multiplied as a correction value to the moving picture image data fed from the memory 32 in order to correct the difference between the moving and still picture image illuminances A and B and to correct the brightness difference between the moving and still picture images displayed on the display 19 in the same manner as the second embodiment. In this embodiment, the same effects and advantages as those of the second embodiment can be obtained.

According to the present invention, the ratio between the moving and still picture image illuminances of the illumination light or the brightness difference between the moving and still picture images can be reduced to at least a certain small value. Further, the present invention is able to utilize discontinuous light pulses located in odd and even fields in the freezing operation.

Although the present invention has been described in its preferred embodiments with reference to the accompanying drawings, it is readily understood that the present invention is not restricted to the above described preferred embodiments, and various changes and modifications may be made in the present invention by those skilled in the art without departing from the spirit and scope of the present invention.

What is claimed is:

1. An endoscope having a scope in which moving and still image pickup operations are alternatively carried out, comprising:
   light source means for selectively emitting a continuous light and a pulsed light in moving and still pickup operations;
   brightness detecting means for detecting brightness of both the continuous light and the pulsed light to obtain brightness signals of both the continuous light and the pulsed light;
   brightness signal processing means for processing both of said continuous light brightness signal and said pulsed light brightness signal to obtain a light control signal; and
   light source controlling means for controlling the luminous energy of said light source means by varying a current of a light valve employed in said light source means in response to said light control signal in order to substantially equalize the brightness of the moving image with the brightness of the still image.

2. The endoscope of claim 1, further including a signal processor for calculating the intensity of the light from the light source during a moving image pickup operation and comparing this intensity to the intensity of the light from the light source during a still image pickup operation, this calculation determining the illumination to be provided to the endoscope during a still operation.

3. The endoscope of claim 2, in which the calculation is compared to a reference value, the intensity of the light from the light source during a still operation being adjusted in response to the comparison.

4. An endoscope having a scope, in which moving and still pickup operations are alternatively carried out, the endoscope comprising:
   light source means for selectively emitting a continuous light and a pulsed light during the moving or still image pickup operations, respectively;
   image pickup means for picking up an endoscopic image of a biological body under medical examination while selectively irradiating said continuous light and said pulsed light thereto, thereby obtaining a moving picture signal and a still picture signal;
   luminous signal producing means for processing said moving image signal and said still image signal to obtain an illuminous ratio A/B between illuminance A of said moving image signal and illuminance B of said still image signal; and
   image signal processing means for processing said moving image signal and said still image signal derived from said image pickup means based upon said illuminous ratio A/B, in order to substantially equalize the brightness of the moving image with the brightness of the still image.

5. The endoscope of claim 4, further comprising means for displaying at least one of the moving and still images.

6. The endoscope of claim 4, wherein the image signal processing means includes means for multiplying a factor representing one of the brightnesses of the moving and still images by a correction value.

7. The endoscope of claim 6, wherein the multiplying means multiplies a correction value by a factor representing the difference between the brightnesses of the moving and still images.

8. The endoscope of claim 4, wherein detecting means includes average operator means for alternately calculating the brightnesses of the moving and still images, first and second latch means for storing the brightnesses of the moving and still images, respectively, and divider means for obtaining the illuminance ratio between the moving and still images.

9. An endoscope having a scope in which moving and still image pickup operations are alternatively carried out, the endoscope comprising:
   light source means for selectively emitting a continuous light or a pulsed light during said moving or still image pickup operations, respectively;
   image pickup means for picking up an endoscopic image of a biological body under medical examination while selectively irradiating said continuous light and said pulsed light thereto, thereby obtaining a moving image signal and a still image signal;
   brightness detecting means for detecting the brightness of both the continuous light and the pulsed light, to obtain brightness signals of both the continuous light and the pulsed light;
   brightness signal processing means for processing both of said continuous light processing signal and said pulsed light brightness signal to obtain an illuminance ratio (A/B) between illuminance (A) of said moving image signal and illuminance (B) of said still image signal; and
   image signal processing means for processing said moving image signal and said still image signal derived from said image pickup means based upon said illuminance ratio (A/B) in order to substantially equalize the brightness of the moving image with brightness of the still image.

10. The endoscope of claim 9, wherein a multiplier receives color correcting information from a signal processor, the signal processor receiving indications of the illumination of an object from a photodetector.

11. The endoscope of claim 10, wherein the signal processor includes a summing means for summing moving and still image signals.

12. The endoscope of claim 11, wherein the signal processor further includes first and second latch means for storing moving and still image signals from the endoscope.

13. The endoscope of claim 12, wherein the signal processor further includes a divider for determining the ratio of illuminances of light provided by the endoscope during moving and still operations, this ratio determining said illumination correcting information.

* * * * *